Nov. 19, 1963 H. B. LEWIS ETAL Plant Pat. 2,312
AZALEA PLANT
Filed Oct. 10, 1962 2 Sheets-Sheet 1
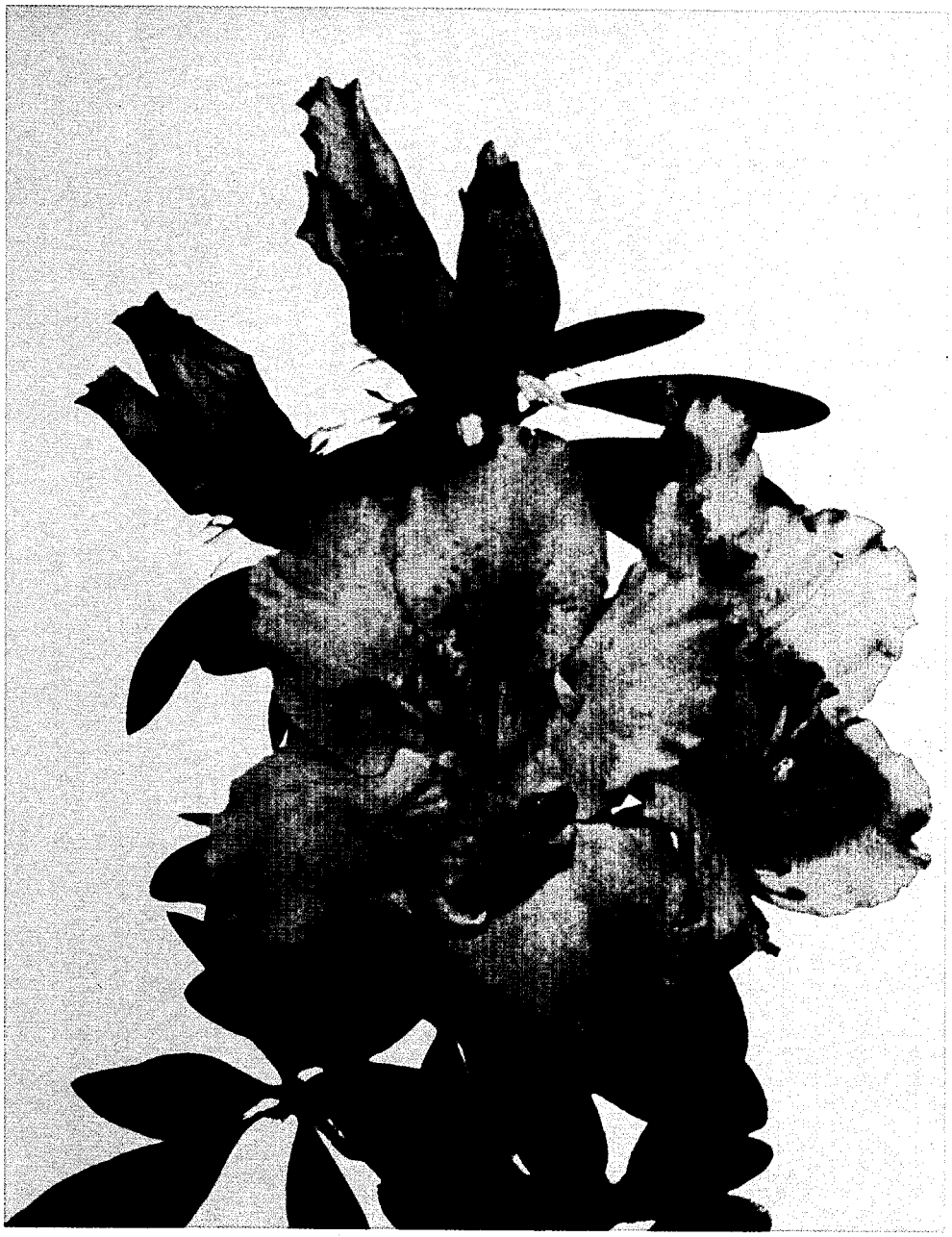
Inventors.
H. B. Lewis and
H. H. Lewis
By: Robb & Robb
Attorneys.

Nov. 19, 1963 H. B. LEWIS ETAL Plant Pat. 2,312
AZALEA PLANT
Filed Oct. 10, 1962 2 Sheets-Sheet 2
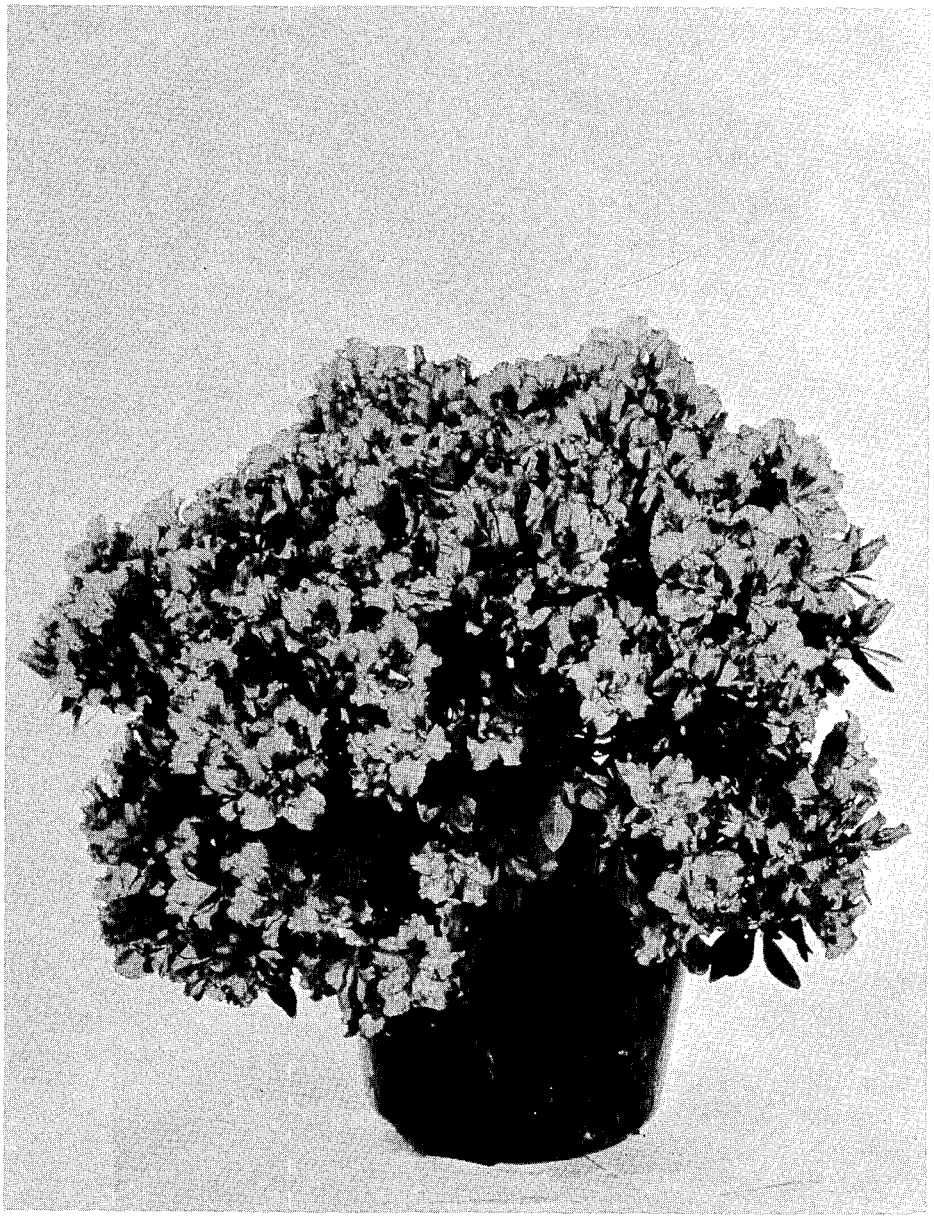
Inventors.
H. B. Lewis and
H. H. Lewis
By: Robb & Robb
Attorneys.

United States Patent Office

Plant Pat. 2,312
Patented Nov. 19, 1963

2,312
AZALEA PLANT

Hubert B. Lewis and Helen H. Lewis, both of
16562 E. Leffingwell Road, Whittier, Calif.

Filed Oct. 10, 1962, Ser. No. 229,773
1 Claim. (Cl. Plt.—57)

The present invention relates to a new and distinct variety of azalea plant which was originated by us by crossing the Belgian Indian variety known as "Miss Cottage Gardens" (unpatented) with the Rutherfordiana variety known as "Firelight" (unpatented), the former being the seed parent and the latter being the pollen parent.

As the result of this breeding, we have produced a new azalea variety which is endowed with a new and improved combination of characteristics, as evidenced by the following features which are outstanding therein and which distinguish the new variety from its parents, as well as from all other varieties of which we are aware:

(1) Strong and upright habits of growth;

(2) Attractive, very dark green and glossy foliage of heavy texture;

(3) Large, bright red flowers; and (4) Suitability for forcing over long seasons, and the ability to be forced into bloom out of season when appropriately pruned.

Our new azalea variety is, in our judgment, the brightest red of all azalea varieties heretofore known. It is much superior to its pollen parent, "Firelight," and has very outstanding foliage. It is a much stronger and upright grower than its seed parent, "Miss Cottage Gardens." Its unique combination of features make it more outstanding than either parent variety, as well as a commercially desirable and important addition to the azalea world.

Asexual reproduction of our new variety by cuttings, as performed at Rivera, California, and at Whittier, California, shows that the foregoing characteristics and distinctions come true to form and are established and transmitted through succeeding propagations.

The accompanying drawings show a typical specimen plant of our new azalea variety as depicted in black and white to illustrate its general form and habit of growth, as well as typical specimens of the flowers and foliage as depicted in color on a somewhat enlarged scale to better illustrate the details thereof.

Locality where grown and observed: Whittier, California.
Propagation: Holds its distinguishing characteristics through succeeding propagations by cuttings.

*Plant*

Form: Much-branched; compact.
Habit: Medium growth; branching; compact.
Rooting habit: Good; easy.
Foliage:

*Size.*—Medium.
*Quantity.*—Normal.
*Color.*—New foliage: upper side—Spinach Green, Plate 0960/1; under side—Scheeles Green, Plate 860/1. Old foliage: upper side—Parsley Green, Plate 00962; under side—Scheeles Green, Plate 860.
*Shape.*—Oval.
*Texture.*—Upper side—glossy; heavy. Under side—smooth.
*Margin.*—Smooth.
*Aspect.*—Good.
*Disease resistance.*—Good resistance to ordinary diseases to which azalea plants are normally subject, as determined by comparison with other varieties grown under the same cultural conditions at Whittier, California.

*Flowers*

Borne: 2 or 3 to stem; regularly arranged on short, strong stems.
Blooming habit: Excellent.
Blooming season: Spring; excellent for forcing.
Quantity of bloom: Abundant, both outdoors and in greenhouse.
Continuity: Heavy during one season, and then intermittent throughout the year. Lasting quality—long.
Petalage: Under normal conditions, has 5 petals, sometimes with a small raised center.
*Color.*—Spiraea Red, Plate 025.
*Texture.*—Heavy.
*Appearance.*—Bright Spiraea Red both inside and out; edges slightly ruffled.
*Shape.*—Semi-double.
*Arrangement.*—5 petals on single flowers, but 5 petals with a very small center on some flowers.
Bud: Slightly ruffled before opening. Color—Spiraea Red, Plate 025.

*Reproductive Organs*

Stamens: From 3 to 6; some attached to flower petals. Color—red.
Pollen: Color—white.
Style: Normal.
Ovaries: Normal.

We claim:

A new and distinct variety of azalea plant, substantially as herein shown and described, characterized particularly as to novelty by the unique combination of strong and upright habits of growth, attractive, very dark green and glossy foliage of heavy texture, large, bright red flowers, and the suitability for forcing over long seasons, as well as the ability to be forced into bloom out of season when appropriately pruned.

No references cited.